United States Patent
Piechaczyk et al.

(10) Patent No.: US 6,426,088 B1
(45) Date of Patent: Jul. 30, 2002

(54) ENCAPSULATED CELLS PRODUCING ANTIBODIES

(75) Inventors: Marc Piechaczyk, Saint Gely du Fresc; Mireia Pelegrin; Mariana Marin, both of Montpellier, all of (FR); Robert Saller, München; Brian Salmons, Markt Indersdorf, both of (DE)

(73) Assignees: Bavarian Nordic Research Institute, Glostrup (DK); Centre National de la Recherche Scientifique, Cedex (FR)

( * ) Notice: Subject to any disclaimer, the term of this patent is extended or adjusted under 35 U.S.C. 154(b) by 0 days.

(21) Appl. No.: 09/331,447
(22) PCT Filed: Dec. 18, 1997
(86) PCT No.: PCT/EP97/07120
§ 371 (c)(1),
(2), (4) Date: Jun. 21, 1999
(87) PCT Pub. No.: WO98/27966
PCT Pub. Date: Jul. 2, 1998

(30) Foreign Application Priority Data

Dec. 23, 1996 (DK) ............................................. 1497/96

(51) Int. Cl.$^7$ ................................................. A61K 9/48
(52) U.S. Cl. ................. 424/451; 424/9.321; 424/9.322; 424/455; 424/457; 424/461; 424/491; 424/499
(58) Field of Search ..................... 264/4.1; 424/9.321, 424/9.322, 320.1, 402.24, 450, 451, 457, 461, 455, 491, 499; 514/44

(56) References Cited

U.S. PATENT DOCUMENTS

| 5,100,673 | A | | 3/1992 | Bader et al. |
| 5,116,747 | A | | 5/1992 | Moo-Young |
| 5,427,935 | A | | 6/1995 | Wang |
| 5,997,900 | A | * | 12/1999 | Wang et al. ................. 424/451 |

FOREIGN PATENT DOCUMENTS

| EP | 88102228.9 | 2/1988 |
| WO | PCT/US96/03666 | 3/1996 |

OTHER PUBLICATIONS

Eisen et al. British J Pharmacology. 42: 383–391, 1971.*
Ledley et al. Pharmaceutical Research. 13: 1595–1614, Nov. 1996.*
Verma et al. Nature. 389: 239–242, Sep. 1997.*
Hughes et al. Human Gene Therapy. 5: 1445–1455, Dec. 1994.*
Merten et al. Cytotechnology. 7(2): 121–130, Oct. 1991.*
Abbas et al. Cellular and Molecular Immunology. 3rd Ed. WB Saunders Co., 1997.*

* cited by examiner

*Primary Examiner*—Dave T. Nguyen
(74) *Attorney, Agent, or Firm*—McCutchen, Doyle, Brown & Enersen

(57) ABSTRACT

The present invention relates to capsules encapsulating antibody-producing cells, and to use of such capsules and encapsulated cells, respectively, for implantation in vivo for long term delivery or sustained delivery of antibodies of therapeutic interest.

47 Claims, No Drawings

ENCAPSULATED CELLS PRODUCING ANTIBODIES

This application is a 35 U.S.C. §371 filing of PCT/EP97/07120 filed Dec. 18, 1997 which claims priority to Danish Application No.: 1497/96 filed Dec. 23, 1996.

The present invention relates to encapsulated cells producing antibodies, especially antibodies belonging to the various classes of immunoglobulines; IgM, IgD, IgGs, IgE and IgA, and to the use of such encapsulated cells for implantation in vivo for long term delivery or sustained delivery of antibodies of therapeutic interest.

BACKGROUND

Systemic delivery of cytostatic or cytotoxic tumor-specific antibodies b y engineered cells grafted to patients may be highly valuable for long-term anticancer surveillance treatments to prevent relapse after a primary treatment such as surgery, chemo- or radiotherapy. Such an approach could also be used for treating severe viral diseases, such as AIDS, if virus-neutralizing antibodies or antibodies toxic for virus-producing cells are delivered. In addition, long-term systemic delivery of antibodies may also be useful for more fundamental purposes such as the development of new animal models of autoimmune diseases in which the humoral response contributes to the development of the illness (Rose, N. R. and Bona, C., Immunol. Today, Vol. 14, 426–430 (1993)). Another possible application involve the development of a new cell ablation technique useful for studying in vivo various differentiation pathways and/or the biological importance of specific cell subsets through the release into the blood stream of cytotoxic antibodies recognizing cell type-specific membrane markers. In this situation, antibodies would kill target cells, for instance after a specific differentiation step, immediately following the appearance of cognate antigens at the surface of the differentiating cells.

It has been recently shown that—by using retroviral gene transfer—several cell types (including skin fibroblasts, myogenic cells, hepatocytes and keratinocytes), amenable to genetic modification and grafting to patients, can produce antibodies retaining the specifity and the affinity of the parental antibody (Noel, D et al., Hum. Gene Ther., Vol. 8, 1219–1229 (1997)). Furthermore, the grafting of engineered myogenic cells allows the systemic delivery of cloned antibodies in mouse for at least several months. Although these observations lend support to the idea that engineering of patients' cells may be useful for long-term antibody-based gene therapies, several issues potentially limit the clinical application of such a technology. First, such a therapeutical approach would be labor-intensive and time consuming. Second, stable genetic modification of patients' cells currently utilises ex vivo retroviral infection followed by autologous grafting in order to avoid rejection of non-MHC (MHC=major histocompatibility complex) matched cells b y the immune system. This reduces the versatility of the approach since engineered cells from one individual cannot be used for another. Third, efficient gene transfer and long-term expression of transgenes in cells that can be used in gene therapy protocols are issues that have not yet been completely solved (Crystal, R. G., Science, Vol. 270, 404–410 (1995); Harris, J. D. and Lemoine, N. R., Trends Genet., Vol. 12, 400–405 (1996); Vile, R. G. et al., Mol. Biotechnol., Vol. 5, 139–158 (1996)).

In this context, implantation of engineered cells encapsulated into immunoprotective devices into patients may represent a more versatile and cost-effective approach. On the one hand, it should allow the same batch of non-MHC-matched cells (possibly selected in vitro for optimal antibody expression) to be used for several patients and, on the other hand, implantation of capsules is a very simple surgical operation. In addition, such a technique would also offer the possibility of easy surgical removal of antibody-producing cells in case the treatment needs to be terminated.

For optimal function, the capsule pores must meet two criteria. First, they must be large enough to permit molecules of interest, such as antibodies, to exit and to permit the entry and efficient diffusion of nutrients necessary for cell survival. Second, they must be small enough to prevent the encapsulated cells from leaving the capsules and to prevent entry of host immune system cells.

Encapsulation of cells in permeable structures that allow the release of certain biologically active molecules but protects the cells producing these molecules from the host immune system has met with some success (for a review see Chang, P. L. In Somatic Gene Therapy. P. L. Chang, ed. (CRC Press, Boca Raton), p 203–223 (1995)). Cells that have been genetically modified to produce human growth hormone (hGH) (Tai, I. T. and Sun, A. M., FASEB J. 7, 1061–1069 (1993)) or a secreted form of human adenosine deaminase (Hughes et al., Hum. Gene Ther. 5, 1445–1455 (1994)) have been encapsulated. In both of these studies, cells were encapsulated in poly-L-lysine-alginate microcapsules and the cells were shown to survive for long periods in culture. This was accompanied by long term production of the enzyme or hormone. Further, it was shown that upon transplantation of the microcapsules into mice, the cells remained viable for 1 year and they continued to produce hGH, demonstrating that the capsules protect the transfected cells from destruction by the host immune system. Nevertheless, it was also reported that polylysine-alginate capsules induce an inflammatory response (Pueyo, M. E. et al., J. Biomater. Sci. Polym. Ed., Vol. 5, 197–203 (1993); Vandenbossche, G. M. et al., J. Pharm. Pharmacol., Vol. 45, 115–120 (1993)).

Cell encapsulation has also been reported using other materials. Baby hamster kidney cells genetically modified to produce nerve growth factor have been encapsulated in polyacrylonitrile/vinyl chloride and implanted in rat brain. The encapsulated cells survived for at least 6 months and continued to produce NGF (Winn et al., Proc. Natl.Acad. Sci. USA 91, 2324–2328 (1994) and Deglon et al., Gene Ther., 2, 563 (1995)).

Rat hybridoma cells secreting a mAb directed against murine IL-4 have been encapsulated in alginate and implanted, intraperitoneally and subcutaneously, into mice (Savelkoul, H. F. et al., J. Immunol. Methods, Vol. 170, 185–196 (1994)). However, the levels of antibody delivered in the blood stream declined after 14 days as a consequence of capsule deterioration. Moreover, in this system a 100% incidence of ascite development was observed 30 days post-implantation as a result of cell released from the capsules into the intraperitoneal cavity.

Hepatocytes have successfully been encapsulated in a polyelectrolyte complex of cellulose sulphate and polydimethyldiallyl ammonium (Stange et al., Biomat.Art.Cells & Immob. Biotech. 21, 3443–352 (1993)). More than 90% of the encapsulated hepatocytes retained their viability and in contrast to hepatocytes grown as monolayers, the encapsulated cells showed an increased metabolic activity.

The same encapsulation materials have been used for the encapsulation of antibody producing hybridoma cells (Merten et al. Cytotechnology 7:121–130, 1991).The capsules were prepared from a solution of sodium cellulose sulphate (1.5%) and poly-dimethyl-diallyl-ammoniumchloride (2% solution). The influence of varying encapsulation process parameters on capsule characteristics, cell growth, and monoclonal antibody production were tested and it was demonstrated that encapsulation using sodium cellulose sulphate as polyanion and poly-dimethyl-diallyl-ammonium-chloride as polycation, is a suitable tool for the preparation capsules useful for the cultivation of mammalian cells at high densities.

To summarize of what is known from the state of the art either in vivo implantation of the encapsulated cells producing antibodies for long term delivery and/or sustained release of antibodies for therapy is not described. or even suggested, or implantation of capsules resulted in severe side effects as, e.g., inflammatory responses.

OBJECT OF THE INVENTION

It is, thus, an object of the present invention to provide capsules containing antibody-producing cells, which allow the release of the antibodies from the capsules, and which do not elicit inflammatory response after implantation in a host.

SUMMARY OF THE PRESENT INVENTION

The present invention then inter alia comprises the following, alone or in combination:

Capsules encapsulating antibody-producing cells, said capsules comprising a core containing said cells and a porous capsule wall surrounding said core which is permeable to the antibodies produced by said cells;

capsules as above wherein said porous capsule wall consist of a polyelectrolyte complex formed from counter-charged polyelectrolytes;

capsules as above wherein said porous capsule wall consist of a complex formed from cellulose sulphate and polydimethyidiallylammonium;

capsules as any above wherein said cells have been genetically modified to produce cloned antibodies;

capsules as any above wherein said antibodies belong to the IgA, IgM, IgG, IgD or IgE classes of immunoglobulins;

capsules as any above wherein said antibodies are selected from antibodies that bind to
    viral surface markers on the surface of virus infected cells,
    cancer cells,
    T- or B lymphocytes involved in the pathological effects of auto-immune diseases,
    surface markers of parasites, or
    circulating antigens with deleterious effects (for example autoantibodies)
and have a cytostatic or cytotoxic effect on said cells, or wherein said antibodies are selected from antibodies that bind to and block viral receptors necessary for viral infection of cells, or direct neutralizing effect via their binding to viruses or direct neutralizing effect on circulating deleterious antigens;

use of the capsules as any above for the implantation into a living animal body, including a human, for the treatment of diseases or disorders responsive to the antibodies released from said capsules;

use as above for subcutaneous implantation;

use of the capsules as any above for producing a pharmaceutical composition for the treatment of diseases or disorders responsive to the antibodies released from said capsules;

a pharmaceutical composition containing capsules as any above for the treatment of diseases or disorders responsive to the antibodies released in a therapeutically effective amount from said capsules;

a method for the treatment of a disorder or disease responsive to the antibodies produced by encapsulated cells as any above comprising implantation of said capsules and/or of the pharmaceutical composition as above into a living animal body, including a human;

a method as above comprising subcutaneous implantation; and a method as above wherein a cancer or an auto-immune disease is treated, or infections by parasites or pathogenic viruses are treated or prevented.

THE INVENTION

According to the present invention, capsules containing cells producing antibodies, which allow the release of the antibodies from the capsules, and which do not elicit inflammatory response after implantation in a host, are provided.

The encapsulated cells according to the invention can be prepared by suspending the cells producing antibodies in an aqueous solution of a polyelectrolyte (e.g. selected from sulphate group-containing polysaccharides or polysaccharide derivatives or of sulphonate group containing synthetic polymers), whereafter the solution in the form of preformed particles is introduced into a precipitation bath containing an aqueous solution of a counter-charged polyelectrolyte (such as for example a polymer with quaternary ammonium groups).

Sulphate group-containing polysaccharides or polysaccharide derivatives includes cellulose sulphate, cellulose acetate sulphate, carboxymethylcellulose sulphate, dextran sulphate or starch sulphate in the form of a salt, especially a sodium salt. The sulphonate group-containing synthetic polymer can be a polystyrene sulphonate salt, preferably a sodium salt.

Polymers with quaternary ammonium groups includes polydimethyldiallylammonium or polyvinylbenzyl-trimethylammonium, in the form of a salt thereof, preferably a chloride salt.

In a preferred embodiment of the invention the cells producing antibodies are encapsulated in a complex consisting of a complex formed from cellulose sulphate and polydimethyidiallyl-ammonium.

Methods for the preparation of the cellulose sulphate capsules used for the preparation of the capsules according to the invention has been thoroughly described in DE A1 40 21 050. Also the synthesis of the cellulose sulphate has been described in this patent application. Methods for a comprehensive characterisation of cellulose sulphate capsules have been extensively dealt with in H. Dautzenberg et al., Biomat., Art. Cells & Immob. Biotech., Vol. 21, 399–405 (1993). Cellulose sulphate capsules and their preparation have also been described in GB 2 135 954. The properties of the cellulose capsules, i.e. the size, the pore size, wall thickness and mechanical properties depend upon several factors such as for example physical circumstances whereunder the capsules have been prepared, viscosity of precipitation bath, its ion strength, temperature, rapidity of addition of celVcellulose sulphate suspension, cnstitution of cellulose sulphate, as well as other parameters described by the Dautzenberg group.

The capsules according to the invention can be prepared by suspending the cells producing antibodies in a solution containing 0.5–50%, preferably 0.5–5%, sodium cellulose sulphate and 5% fetal calf serum in an aqueous solution, preferably a buffer. This suspension is then dropped by a dispensing system (e.g. air-jet system or piezoelectric system) into a precipitation bath containing a stirred solution of 0.5%–50%, preferably 0.5–10% polydimethyldiallylammonium chloride in an aqueous solution, preferably a buffer. Capsule formation occurs within milliseconds and the capsules containing cells are kept in the precipitation bath for 30 seconds to 5 minutes and then washed. The rapidity of this method ensures that the cells are not unduly stressed during the whole procedure (Stange et al., Biomat. Art. Cells & Immob. Biotech. 21. 343–352 (1993)).

The capsules according to the invention have a variable diameter between 0.01 and 5 mm, but are preferably between 0.1 and 3 mm. Consequently, capsules can be made to contain a variable number of cells. Using the encapsulation process according to the invention, up to $10^{10}$, but preferably $10^3$–$10^7$ cells producing antibodies can be encapsulated in the polyelectrolyte complex.

Capsules composed of cellulose sulphate and polydimethyldiallyl ammonium have excellent mechanical properties and can be manufactured to consistent diameter and pore size.

The encapsulated cells can be cultivated in a normal cell culture medium (the nature of which depends on the encapsulated cells) at standard conditions of humidity, temperature and $CO_2$ concentration. During this culture period production of antibodies from the capsules into the cell culture medium can be demonstrated with either Western Blot or Elisa technology using specific antigens and can furtheron be quantitated using second antibodies conjugated to fluorogenic dyes.

After a suitable period in culture (normally not less than 1 hour and not exceeding 30 days), the cell containing capsules can be surgically implanted either directly, or by injection using a syringe into various areas of the body.

The antibodies produced by the encapsulated cells according to the invention can be based on any immunglobulin class useful for therapy, including but not limited to genetically modified antibodies.

The encapsulated cells according to the invention can be cells taken from patients or from any other source, including human and animal cells, that have been genetically modified for the production of cloned antibodies.

The encapsulated cells and capsules, respectively, are especially used for the implantation into a living animal body, including a human, for the treatment of diseases or disorders responsive to the antibodies released from said capsules. After implantation of capsules into an animal body intraperitoneally and subcutaneously it has been found that the capsules, especially cellulose sulphate capsules, offer an obvious advantage with respect to mechanical resistance over, for instance, alginate capsules since there are found intact as long as 10 months post-implantation regardless of whether they are implanted subcutaneously or intraperitoneally.

Additionally, it has been observed that subcutaneous and intraperitoneal implantations of cell-containing cellulose sulphate capsules revealed differences with respect to at least two points. First, the amount of antibody released in the bloodstream was markedly higher in the former situation. A very likely explanation for this difference resides in the fact that capsules are rapidly vascularized when implanted subcutaneously and are not vascularized at all when implanted intraperitoneally. The beneficial effect of vascularization might be two-fold, firstly facilitating antibody uptake by blood and, secondly, ensuring a better supply of nutrients favoring cell survival since viability of cells within intraperitoneally implanted capsules was reproducibly observed to be lower. In addition to extensive vascularization, which showed no significant alteration over the 10 months of the follow-up, the clustering of cells within a connective pouch after subcutaneous implantation would allow removal of capsules through an easy onestep surgical ablation of the whole neorgan should this prove necessary. Finally, it is important to underline that development of isolating fibrosis around implanted cellulose sulphate capsules is not systematic. This observation contrasts with what has been reported in the case of alginate-poly(L)-alginate microcapsules around which a host reaction with fibrosis developed probably as a result of potent macrophage activation by the encapsulating polymer (Pueyo, M. E, et al., J. Biomater Sci. Polym. Ed., Vol. 5, 197–203 (1993)).

Anti-idiotypic response are often observed in patients repeatedly treated with high doses of purified monoclonal antibodies and can sometimes neutralize the effects of the treatment (Isaacs, J. D., Semin. lmmunol., Vol. 2, 449–456 (1990)). Moreover, the mode of administration of antibodies has also been shown to be a crucial parameter with regard to the induction of anti-idiotypic responses. For example, subcutaneous and intradermal injections have been reported to be much more immunogenic than intravenous injection (Durrant, L. G. et al., Cancer Immunol. Immunother., Vol. 28, 37–42 (1989)). It is thus important to underline that no detectable anti-idiotypic response against monoclonal antibodies developed in animal bodies implanted with cellulose sulphate encapsulated cells releasing said antibodies has been observed.

To summarize, the data presented above clearly demonstrate that implantation of encapsulated cells releasing antibodies is suitable for long-term antibody-based gene/cell therapy approaches, especially directed against cancers and viral diseases.

Accordingly, in a preferred embodiment of the invention, the encapsulated antibody-producing cells are used in therapy where a sustained release of antibodies on a long term treatment is necessary.

Such situations are for example diseases caused by chronic virus infection, such as HIV, Hepatitis B, Herpes simplex, and Herpes genitalis.

Certain, viral infections result in the exposition of specific markers or antigens at the cell surface. Such surface markers can be selectively recognised by specific antibodies which can be modulated to be toxic for the virus-infected cells. Encapsulated cells producing such antibodies can be applied for long-term treatments of viral infections.

In an other embodiment of the invention, encapsulated cells producing neutralising antibodies which recognise and bind to markers or viral receptors on the cell surface interacting with viruses in the initial phases of viral infection, providing an direct or indirect neutralising effect on the a viral infection, are provided.

Neutralising effects may in this case rely on a direct block in binding and/or cell entry of the virus and thereby prevent further infection of any target cell or indirect on lysis by the patients own complement system or on presenting the virus via antibodies to cells of the immunosystem such as monocytes or macrophages.

In a special embodiment, the invention relates to the use of the encapsulated cells according to the invention in the treatment of tumours.

In any situation in which a specific cell type, or a specific cell subset capable of self renewal turns out to be toxic or life threatening for human beings, cell specific toxic antibodies, normal or genetically modified improving its toxicity, produced by encapsulated cells for selective destruction of cells can be used for elimination of tumour cells.

An other application of the capsules according to the invention is in the treatment severe autoimmune diseases, such as Multible Sclerosis and Rheumatic Arthritis, where specific T- and B-cells responsible for the pathological effect can be constantly eliminated in long term treatments by cell-specific toxic antibodies produced by encapsulated cells In a further embodiment of the invention, encapsulated cells producing antibodies against surface markers of parasites such as *Plasmodium falciparum, P. vivax* or *P. malariae* are provided.

Malaria is one of the three diseases that cause most deaths a year, beside TBC and HepB. The application of antibodies against Plasmodium with the consequence of marking the parasites and thereby attracting cells of the immunsystem to destroy the parasites could be used as a non toxic non harmful prophilaxis for travellers to countries with a high risk of Malaria infection.

The encapsulated, antibody-releasing cells can also be used for producing a pharmaceutical composition containing a therapeutically effective amount of the cells together with at least one pharmaceutical carrier or diluent.

The following examples will illustrate the invention further but are not to be constructed as limiting:

EXAMPLE

Cells and Cell Culture Conditions

The hybridoma cell line, Tg 10, prepared by fusion of mouse myeloma cells (P3-X63-Ag8.653) with spleen cells from mice immunised with hTg (Piechaczyk, M. Chardes, T., Cot, M. C., Pau, B., and Bastide, J. M., Hybridoma, Vol 4, No. 4, 361–67 (1985)). was used for encapsulation. Tg 10 cells produce a monoclonal antibody (mAb), also named Tg 10, against human thyroglobulin. Cells were grown in RPMI 1640 (Gibco/BRL) supplemented with 10% FCS in the presence of 100 u.(=Units)/ml streptomycin, 100 u./ml penicillin and 2 mM L-glutamine. Tg10 cells encapsulated in the cellulose sulphate matrix (CSM) were cultured under the same conditions as free cells.

Antibody and F(ab)'2 Fragments Purification

Tg10 mAb was purified for Tg10 cell culture supernatant by affinity chromatography (Durrant, L G et al., Cancer Immunol. Immunother., Vol. 28, 37–41 (1989)). Rabbit antiidiotypic antibody against the Tg10 mAb was produced as described (Del Rio, M. et al., Immunol. Invest., Vol. 24, 655–667 (1995)). Tg10 F(ab)'2 fragment was prepared electrophoretically after cleavage of Tg 10 mAb by pepsin and purity of preparations were controlled by SDS-PAGE analysis (Del Rio, M. et al., Immunol. Invest., Vol. 24, 655–667 (1995)).

Cell Encapsulation $10^7$ cells were suspended in 1 ml of a buffered saline solution containing 3,8% sodium cellulose sulphate and 5% fetal calf serum. The suspension was dropped into a precipitation bath containing 2,5% poly-dimethyl-diallylammonium (PDDMDAAC) in buffered saline using a dispensing system (air-jet system). Capsule formation occurred within milliseconds followed by further constitution of an inner, more porous, layer for mechanical support essentially consisting of cellulose sulphate. The capsules containing cells are kept in the precipitation bath for 30 seconds to 5 minuntes and then washed in DMEM (Stange et al., Biomat.Art.Cells & Immob. Biotech. 21, 3443–352 (1993)).

Batches obtained to different parameters as described above, i.e. concentration of sodium cellulose sulphate, flow of air-jet system and time in precipitation bath were used for biological studies. Representative examples of conditions are for example: 2.5% sodium cellulose sulphate, 2% polydimethyl-diallylammonium, and 1 minute in precipitation bath, or 1.5% sodium cellulose sulphate, 2% polydimethyl-diallylammonium, and 0.5 minute in precipitation bath, or 3% sodium cellulose sulphate, 3% polydimethyl-diallylammonium, and 2 minute in precipitation bath. The exact parameters can be selected also taking into account the exact size of the capsules wanted, the thickness of the capsule wall as well as other properties.

Implantation of Capsules

Four to six week-old C3 H mice (IFFA-CREDO) were anaesthesized using 0.01 ml per gram of body weight of a solution containing 0.1% Xylazine (Rompun, Bayer) and 10 mg/ml Ketamine (Imalgene, Rhone Merieux). Capsules were washed in phosphate buffered saline (0.15 M NaCl, 0.01 M Na phosphate pH 7) before implantation. Six or twenty CSM-Tg10 capsules were implanted into mice either intraperitoneally or subcutaneously (abdominal zone). In the latter case, they were implanted at one or three sites in clusters of six or seven capsules per site.

Mice Immunization

For generating Tg10 anti-idiotypic antibodies, six week-old B6D2F1 females (IFFA CREDO) were injected intradermally at multiple sites using 20 μg per mouse of purified Tg10 mAb emulsified in a 1:1 volume ratio of complete Freund's adjuvant (Sigma). Two booster injections of 20 jig of purified Tg10 mAb. (10 μg intraperitonelly and 10 μg intramuscularly) in incomplete Freund's adjuvant (Sigma) were given three and four weeks after the first immunization, respectively. Mice were bled before each immunization and one week after the last one. After clotting, blood samples were centrifuged at 6000 rpm for 15 minutes and serum aliquots were stored at −20° C. until use. Each serum sample was assayed for the presence of anti-idiotypic antibody against Tg10 as described below.

Immunoassay of Tg10 Antibodies. Analysis of the Anti-idiotypic Immune Response

Tg10 antibodies in cell culture supernatants and in mouse sera were assayed by ELISA using human thyroglobulin (hTg) (UCB-Bioproducts) for the coating of microtiter plates (Maxisorb, Nunc) as described (Piechaczyk, M. et al., Hybridoma, Vol. 4, 361–367 (1985); Noel, b. et al., J. Immunol. Meth., Vol. 193, 177–187 (1996)) and absorbance at 450 nm was measured using the automated MR5000 plate reader from Dynatech. Protein A sepharose-purified Tg10 mAb was used as a standard for concentration determination. Anti-idiotypic antibodies against the Tg10 mAb were assayed by ELISA using Tg10 F(ab)'2 for the coating of microtiter plates (Del Rio, M et al., Immunol. Invest., Vol. 24, 655–667 (1995)). A rabbit antiidiotypic antiserum (Del Rio, M et al., Immunol. Invest., Vol. 24, 655–667 (1995)) against the Tg10 mAb was included in the experiments as a positive control.

In vitro Antibody Production by Tg10 Cells Encapsulated Into Cellulose Sulphate (CS)

At first, it was determined whether the encapsulation process and the CS matrix could be toxic for Tg10 hybridoma cells or could affect antibody production. Encapsulated cells, placed in cell culture conditions, were counted at various time points post-encapsulation after crushing of capsules. Cell viability was controlled using the trypan blue exclusion method. In parallel, Tg10 mAb production was assayed by ELISA. The culture medium was replaced every 24 hours.

The main observations were the following:

(i) each capsule, the diameter of which varies from 0,5 to 2 mm with an average of 1 mm, contained a mean of $2 \times 10^4$ Tg10 cells at the moment of encapsulation, (ii) the viability of encapsulated cells 4 days post-encapsulation was estimated to be at least 80%, (iii) production of the Tg10 mAb was detectable over a period of 50 days, (iv) an initial increase in antibody production lasting 10 days was observed and correlated with limited proliferation of Tg10 cells within capsules (which cannot exceed one or two rounds of division because of space limitations), (v) a marked drop in antibody production, which correlated with the onset of cell death, began between day 10 and day 20.

Taken together, these data indicate that the encapsulation process per se is not toxic for Tg10 cells. Rather, cell survival within the CS matrix seems favoured since Tg10 cells cultured in parallel under standard culture conditions but without passage died within 1 to 2 weeks.

In vivo Delivery of Tg10 mAb after Implantation into Mice of Tg10 Cell-containing CS-capsules Next, it was addressed whether systemic delivery of the Tg10 mAb could be achieved after implantation of capsules into mice. Both, subcutaneous (abdominal zone) and intraperitoneal implantations were tested to determine which localization would allow better delivery of antibodies into the bloodstream. Three C3H mice were implanted intraperitoneally with six capsules and one mouse with 20 capsules. Similarly, three mice were implanted subcutaneously with six capsules and three mice with 20 capsules. Tg10 antibody concentration in the bloodstream was subsequently monitored by ELISA.

It could be observed that antibody production (i) was directly correlated to the number of capsules implanted, (ii) reached a peak between the second and third week post-implantation, (iii) was reproducibly higher when capsules were implanted subcutaneously since it could reach a value as high as 12.5 $\mu$g/ml as compared to 2.5 $\mu$g/ml in the case of intraperitoneal implantation, (iv) could be detected for as long as 4 months although Tg10 antibody concentration in the blood progressively dropped down to only several ten of ng/ml.

Finally, the decrease in antibody production seems to be linked to progressive death of encapsulated cells. Viability of encapsulated cells in capsules removed from mice 2 months post-subcutaneous implantation was estimated to be 20–30%, a value which correlated with the reduction of antibody concentration.

Follow-up of Vascularization of Capsules

Capsules implanted intraperitoneally and subcutaneously behaved different with regard to their vascularization. Thus, 2 months post-implantation, subcutaneoulsy implanted capsules appeared wrapped in a vascularized pouch made up of lax connective tissue. Formation of such neorgans occured regardless of whether capsules contained hybridoma cells or not. In contrast, when capsules were implanted intraperitoneally, they did not form clusters but remained mobile and no vascularization was observed.

Next, onset of vascularization has been investigated, and it has been examined whether the treatment of capsules with angiogenic factors could accelerate and/or improve the vascularization of subcutaneously implanted capsules. Capsules treated with bFGF, a growth factor long known to have angiogenic activity (Montesano, R. et al., Proc. Natl. Acad. Sci. USA, Vol. 83, 7297–7301 (1986);

Thompson, J. A. et al., Proc. Natl. Acad. Sci. USA, Vol. 86, 7928–7932 (1989)) and/or type I rat collagen (Sigma), as described above, were implanted and followed with respect to their vascularization. No obvious difference was observed between the various experimental conditions tested. Blood vessels developing around capsules were easily visible three days post-implantation, and complete vascularization reached after 2 to 3 weeks with a network of blood vessels being present both around and within the neorgan remaining stable for at least 10 months.

No Detectable Inflammatory Response Developed at the Level of Implanted Tg10 Cell-containing CS-capsules Mice were examined for the development of possible inflammatory responses triggered by implanted capsules. No macroscopically detectable immediate or delayed inflammatory response was observed in the vicinity of capsules, either after intraperitoneal or subcutaneous implantation. Also noteworthy was the lack of change in the vascularization of capsules even 10 months after subcutaneous implantation.

Anti-idiotypic Humoral Response Against the Tg10 Antibody Released by Encapsulated Cells was not Detectable The possibility that a humoral response against the Tg10 antibody had developed in mice implanted with encapsulated hybridoma cells was also investigated. A previously characterized rabbit serum containing anti-Tg10 antibodies (Del Rio, M et al., Immunol. Invest., Vol. 24, 655–667 (1995)) was used as a positive control for these experiments. Additionally, a series of mice was immunized with the purified monoclonal antibody in the presence of Freund's adjuvant, as described above. Of thirteen mice injected, six developed a clear anti-idiotypic response indicating that mice are not intrinsically refractory to induction of such a response. In contrast, no anti-idiotypic response was detected in any of the mice implanted with capsules regardless of the blood concentration of antibody and the site of implantation. These data indicate that cellulose sulphate matrix does not exert any obvious adjuvant effect that would have favoured the induction of a neutralizing humoral response against the Tg10 antibody.

To summarize, it has been shown that cellulose sulphate capsules containing hybridoma cells can be used for delivering monoclonal antibodies into the blood stream of immunocompetent mice for at least several months when implanted subcutaneously or in the intra-peritoneal cavity. The above presented data indicate that implantation of capsules containing antibody-producing cells into patients can potentially permit systemic long-term delivery of antibodies and can, thus, be useful in the development of surveillance treatments for cancers and severe viral diseases. Additionally, encapsulation of antibody-producing cells into cellulose sulphate are useful in antibody-based gene/cell therapy approaches.

What is claimed is:

1. A method for sustained delivery of antibodies in an animal, without inflammation, said method comprising:

implanting a capsule containing antibody producing cells in said animal, wherein said capsule is formed from a sulphate group-containing polyanion and a polycation; wherein said implantation of said capsule (i) results in sustained delivery of said antibodies and (ii) wherein said capsule material does not elicit an inflammatory response after implantation into an animal body.

2. The method of claim 1, wherein said polycation is a polymer with quaternary ammonium groups.

3. The method of claim 2, wherein said polycation with quaternary ammonium groups is polydimethyldiallylammonium or polyvinylbenzyl-trimethylammonium.

4. The method of claim 3, wherein said polycation with quaternary ammonium groups is polydimethyldiallylammonium.

5. The method of claim 1 wherein said sulphate group-containing polyanion is cellulose sulphate and said polycation is polydimethyldiallylammonium.

6. The method of claims 1, 2, 3, 4 or 5 wherein said polycation is in the form of a salt.

7. The method of claim 1, wherein said antibody-producing cells have been genetically modified.

8. The method of claim 7, wherein said antibody-producing cells have been genetically modified to produce cloned antibodies.

9. The method of claim 8, wherein said antibody produced by said encapsulated antibody-producing cells binds to a viral cell surface marker, a cancer cell, a T- or a B lymphocytes involved in the pathological effects of an auto-immune disease, a surface marker of a parasite or a deleterious circulating antigen.

10. The method of claim 9, wherein said antibody has a neutralizing effect.

11. The method of claim 1, wherein said implantation step comprises subcutaneous implantation.

12. The method of claim 1, wherein said implantation step comprises intraperitoneal implantation.

13. The method of claim 1, wherein said sulphate group-containing polyanion is selected from the group consisting of a sulphate group-containing polysaccharide and a sulphate group-containing polysaccharide derivative.

14. The method of claim 13, wherein said sulphate group-containing polysaccharide or sulphate group containing polysaccharide derivative is selected from the group consisting of cellulose sulphate, cellulose acetate sulphate, carboxymethyl cellulose sulphate, dextran sulphate and starch sulphate.

15. The method of claim 14 wherein said sulphate group-containing polysaccharide is cellulose sulphate.

16. The method of claims 1, 13, 14 or 15, wherein said sulphate group-containing polyanion is in the form of a salt.

17. The method of claim 16, wherein said salt is a sodium salt.

18. The method of claim 1, wherein said capsule is implanted in combination with at least one pharmaceutical carrier or diluent.

19. The method of claim 1 wherein said antibodies are selected from the group consisting of IgA, IgM, IgG, IgD and IgE classes of imunoglobulins.

20. A pharmaceutical composition comprising a cellulose sulphate capsule containing antibody producing cells, wherein said capsule is formed from a cellulose sulphate polyanion and a polycation, and additionally comprises at least one pharmaceutical carrier or diluent and wherein said cellulose sulphate capsule containing antibody producing cells does not elicit an inflammatory response after implantation into an animal body.

21. The pharmaceutical composition of claim 20, wherein said sulphate group-containing polyanion is cellulose sulphate and said polycation is polydimethyldiallylammonium.

22. A method for sustained delivery of antibodies in an animals without inflammation, said method comprising:
implanting a cellulose sulphate capsule containing antibody producing cells in said animal, wherein said capsule is formed from a cellulose sulphate polyanion and a polycation; wherein said implantation of said capsule (i) results in sustained delivery of said antibodies and (ii) wherein said cellulose sulphate capsule material does not elicit an inflammatory response after implantation into an animal body.

23. The method of claim 22, wherein said polycation is a polymer with quaternary ammonium groups.

24. The method of claim 23, wherein said polycation with quaternary ammonium groups is polydimethyldiallylammonium or polyvinylbenzyl-trimethylammonium.

25. The method of claim 24, wherein said polycation with quaternary ammonium groups is polydimethyldiallylammonium.

26. The method of claims 22, 23, 24 or 25 wherein said polycation is in the form of a salt.

27. The method of claim 26, wherein the salt is a chloride salt.

28. The method of claim 22, wherein said cellulose sulphate polyanion is in the form of a salt.

29. The method of claim 28, wherein said salt is a sodium salt.

30. The method of claim 22, wherein said antibody-producing cells have been genetically modified to produce cloned antibodies.

31. The method of claim 22, wherein said antibody-produced by said encapsulated antibody-producing cells binds to a viral cell surface marker, a cancer cell, a T- or a B lymphocytes involved in the pathological effects of an auto-immune disease, a surface marker of a parasite or a deleterious circulating antigen.

32. The method of claim 31, wherein said antibody has a neutralizing effect.

33. The method of claim 22 wherein said antibodies are selected from the group consisting of IgA, IgM, IgG, IgD and IgE classes of imunoglobulins.

34. A method for sustained delivery of antibodies in an animal, without inflammation, said method comprising:
implanting a capsule containing antibody producing cells in said animal, wherein said capsule is formed from a sulphonate group-containing polyanion and a polycation; wherein said implantation of said capsule (i) results in sustained delivery of said antibodies and (ii) wherein said capsule material does not elicit an inflammatory response after implantation into an animal body.

35. The method of claim 34, wherein said sulphonate group-containing synthetic polymer is a polystyrene sulphonate salt.

36. The method of claim 34, wherein said sulphonate group-containing polyanion is a sulphonate group-containing synthetic polymer.

37. The method of claims 34 or 36 wherein said sulphonate group-containing polyanion is in the form of a salt.

38. The method of claim 37, wherein said salt is a sodium salt.

39. The method of claim 34, wherein said polycation is a polymer with quaternary ammonium groups.

40. The method of claim 39, wherein said polycation with quaternary ammonium groups is polydimethyldiallylammonium or polyvinylbenzyl-trimethylammonium.

41. The method of claims 34, 39 or 40 wherein said polycation is in the form of a salt.

42. The method of claim 41, wherein the salt is a chloride salt.

43. The method of claim 34, wherein said antibody produced by said encapsulated antibody-producing cells binds to a viral cell surface marker, a cancer cell, a T- or a B lymphocytes involved in the pathological effects of an auto-immune disease, a surface marker of a parasite or a deleterious circulating antigen.

44. The method of claim 43, wherein said antibody has a neutralizing effect.

45. The method of claim 34, wherein said antibody-producing cells have been genetically modified to produce cloned antibodies.

46. The method of claim 34 wherein said antibodies are selected from the group consisting of IgA, IgM, IgG, IgD) and IgE classes of imunoglobulins.

47. the method of claim 6, wherein said salt is a chloride salt.

* * * * *